United States Patent [19]
Halpern et al.
[11] Patent Number: 5,043,054
[45] Date of Patent: Aug. 27, 1991

[54] PROCESS FOR DEHALOGENATION OF CONTAMINATED WASTE MATERIALS

[75] Inventors: Yuval Halpern, Skokie; Arthur J. Friedman, Deerfield, both of Ill.

[73] Assignee: Chemical Waste Management, Inc., Oak Brook, Ill.

[21] Appl. No.: 520,732

[22] Filed: May 9, 1990

[51] Int. Cl.[5] ........................ C07C 37/68; C10G 17/00

[52] U.S. Cl. ................................ 208/262.5; 585/469; 585/641; 585/733

[58] Field of Search ..................... 208/262.5; 585/469, 585/641, 733

[56] References Cited

U.S. PATENT DOCUMENTS

| | | | |
|---|---|---|---|
| 4,327,027 | 4/1982 | Howard et al. | 208/262.5 |
| 4,337,368 | 6/1982 | Pytlewski et al. | 208/262.5 |
| 4,351,978 | 9/1982 | Hatano et al. | 208/262.5 |
| 4,353,793 | 10/1982 | Brunelle | 208/262.5 |
| 4,387,018 | 6/1983 | Cook et al. | 208/262.5 |
| 4,400,552 | 8/1983 | Pytlewski et al. | 208/262.5 |
| 4,430,208 | 2/1984 | Pytlewski et al. | 208/262.5 |
| 4,447,541 | 5/1984 | Peterson | 208/262.5 |
| 4,602,994 | 7/1986 | Pytlewski et al. | 208/262.5 |
| 4,663,027 | 5/1987 | Mendiratta et al. | 208/262.5 |
| 4,748,292 | 5/1988 | Mendiratta | 208/262.5 |
| 4,761,221 | 8/1988 | Rossi et al. | 208/262.5 |
| 4,764,256 | 8/1988 | Way | 208/262.5 |
| 4,839,042 | 6/1989 | Tumiatti et al. | 208/262.5 |

*Primary Examiner*—Helane E. Myers
*Attorney, Agent, or Firm*—Allegretti & Witcoff, Ltd.

[57] ABSTRACT

An improved method for detoxifying waste materials contaminated with halogenated hydrocarbons is disclosed. The method achieves dehalogenation of such halogenated hydrocarbons in a manner as efficient as previous methods, but at a considerably lower cost. The economic advantages of the present invention arise from the use of lower temperatures and/or smaller quantities of reagents, which in turn are made possible by the discovery of a surprisingly superior reagent, 2-methoxyethanol.

4 Claims, No Drawings

PROCESS FOR DEHALOGENATION OF CONTAMINATED WASTE MATERIALS

BACKGROUND OF THE INVENTION

1. Field of the Invention

The present invention relates to processes for dehalogenating waste or contaminated materials containing halogenated organic compounds, such as transformer oils, dielectric fluids, wood preservatives, halogenated by-products from the manufacture of halogenated herbicides and soils contaminated with discharges of these materials.

2. Information Disclosure Statement

Polychlorinated biphenyls (PCBs) have shown great utility for use in dielectric fluids, due to their outstanding thermal stability, resistance to oxidation and chemical agents, as well as excellent electrical insulating qualities. However, the discovery of PCBs in environmental samples and subsequent recognition of their potential toxic hazards resulted in restricted sales of PCBs to applications in closed electrical systems, and ultimately to the termination of PCB production in 1977.

PCBs represent only one of a large number of halogenated organic compounds that are currently stored for want of an economical and effective means of disposal. Storage of such chemicals, however, is only a stopgap measure. Storage capacity is not unlimited and the quantity of hazardous chemicals generated by industry continuously increases. Thus, effective and affordable methods for destroying halogenated organic compounds are needed.

The difficulty in decomposing halogenated organic compounds arises from the great stability of the carbon-halogen covalent bond. The energy of a carbon-chlorine bond, for example, is on the order of 84 kcal/mole. Thus, many halogenated organic compounds resist biodegradation as well as most chemical decomposition methods. Most known chemical methods achieve only partial dehalogenation, and involve the use of expensive reagents, inert atmospheres, elevated temperatures, complex apparatus, substantial energy consumption or other undesirable parameters. Physical means of disposal have similar problems. Incineration requires substantial energy consumption and complex equipment and may form residual ash, which may require additional treatment.

Thus, there is a need for effective and economical processes for the decomposition of halogenated organic compounds. Chemical processes have shown some promise for such applications. An ideal chemical process would allow very substantial dehalogenation of halogenated hydrocarbons at low cost, using limited reagent, time and energy resources.

The problems associated with disposal of halogenated organic compounds are well known in the art. Chemical processes for dehalogenation of various hydrocarbons have been described.

Howard et al., U.S. Pat. No. 4,327,027, describes a method for chemical detoxification of toxic chlorinated aromatic compounds comprising incubation of such compounds at elevated temperatures with an amount, in excess of stoichiometric, of alkali metal alcoholates of alkanols, alkoxyalkane glycols, alkanepolyols and monoalkyl ethers thereof.

Pytlewski et al., U.S. Pat. No. 4,349,380 discloses methods for recovering metals from chemically combined forms through the use of alkali metals with polyglycols with at least 4 carbon atoms or polyglycol monoalkyl ethers with at least 5 carbon atoms, and oxygen.

Pytlewski et al., U.S. Pat. No. 4,337,368 relates to the use of alkali metals with polyglycols with at least 4 carbon atoms or polyglycol monoalkyl ethers with at least 5 carbon atoms and oxygen to decompose halogenated organic compounds.

Hatano et al., U.S. Pat. No. 4,351,978 relates to a method for dechlorination of PCB via hydrogenation, and employing an alkaline aqueous/alcohol solution, molecular hydrogen and a hydrogenation catalyst.

Brunelle et al., U.S. Pat. No. 4,353,793 discloses a method for removing PCBs from contaminated nonpolar organic solvents using monocapped polyalkyleneglycol alkyl ethers with alkali metal hydroxides.

Cook et al., U.S. Pat. No. 4,387,018 describes a method for extracting PCBs from oil using methanol.

Pytlewski et al., U.S. Pat. No. 4,400,552 discloses a method for decomposing halogenated organic compounds using a reagent comprising the product of the reaction of an alkali metal hydroxide with a polyglycol with at least 4 carbon atoms or a polyglycol monoalkyl ether with at least 5 carbon atoms.

Pytlewski et al., U.S. Pat. No. 4,417,977 relates to methods for removing halogenated organic compounds from organic functional fluids through the use of alkali metals with polyglycols with at least 4 carbon atoms or polyglycol monoalkyl ethers with at least 5 carbon atoms and oxygen.

Pytlewski et al., U.S. Pat. No. 4,430,208 describes a three step process for the removal and detoxification of PCBs from contaminated dielectric fluids. The process comprises extraction with polyethylene glycol followed by extraction with cyclohexane, followed by incubation with a reagent derived from the reaction of sodium or sodium hydroxide, polyethylene glycol and oxygen.

Peterson, U.S. Pat. No. 4,447,541 discloses a method for reducing the halogen content of highly-halogenated organic soil contaminants through the use of an alkali reagent, such as an alkali metal hydroxide, an alkali metal hydroxide/alcohol or glycol mixture, or an alkoxide, in conjunction with a sulfoxide catalyst.

Tundo, U.S. Pat. No. 4,632,742 discusses a method for decomposing halogenated organic compounds through an anaerobic process using Nixolens (R), alcohols, polyethylene glycols or polyglycol monoalkyl ethers with at least 5 carbon atoms, together with an oxidizing agent.

Weitzman, U.S. Pat. No. 4,662,948 relates to a method for removing PCBs and dioxins from soils through extraction of soils with a mixture of halogenated hydrocarbons and a polar solvent.

Pytlewski et al., U.S. Pat. No. 4,460,797 discloses a method for the decomposition of halogenated organic compounds using a reagent comprising the product of the reaction of an alkali metal hydroxide with a polyglycol with at least 4 carbon atoms or a polyglycol monoalkyl ether with at least 5 carbon atoms.

Pytlewski et al., U.S. Pat. No. 4,471,143 relates to a composition of matter in liquid form comprising a coordination complex which is the product of the reaction of an alkali metal or alkali metal hydroxide with a polyglycol with at least 4 carbon atoms or a polyglycol monoalkyl ether with at least 5 carbon atoms.

Heller, U.S. Pat. No. 4,483,716 discusses processes for removing chemical substances, including halogenated organic compounds, from porous substrates, using a poultice comprising particulate matter and a volatile solvent, then destroying such halogenated hydrocarbons using the product of the reaction of an alkali metal or alkali metal hydroxide with a polyglycol with at least 4 carbon atoms or a polyglycol monoalkyl ether with at least 5 carbon atoms.

Pytlewski et al., U.S. Pat. No. 4,523,043 relates to reagents and methods for decomposition of organic sulfur-containing compounds through the cleavage of carbon-sulfur bonds using the product of the reaction of an alkali metal or alkali metal hydroxide with a polyglycol with at least 4 carbon atoms or a polyglycol monoalkyl ether with at least 5 carbon atoms.

Pytlewski et al., U.S. Pat. No. 4,602,994 discloses a method for the removal of halogenated organic compounds from organic functional fluids using, in an inert atmosphere, the product of the reaction of an alkali metal or alkali metal hydroxide with a polyglycol with at least 4 carbon atoms or a polyglycol monoalkyl ether with at least 5 carbon atoms.

Mendiratta et al., U.S. Pat. No. 4,663,027 relates to a method for removing polyhalogenated hydrocarbons from nonpolar organic solutions by admixing flakes or pellets of an alkali metal hydroxide with such a solution to form a slurry of alkali metal hydroxides of uniform size, followed by reacting such slurry with a polyalkylene glycol or a monocapped polyalkylene glycol alkyl ether.

Mendiratta et al., U.S. Pat. No. 4,748,292 discloses a method for removing polyhalogenated hydrocarbons from nonpolar organic solutions, which uses, in an amount at or exceeding stoichiometric to the total number of halogen groups, a reagent comprised of an alkali metal hydroxide and a polyalkylene glycol or a monocapped polyalkylene glycol alkyl ether.

Way, U.S. Pat. No. 4,764,256 describes a method for the removal of PCBs from contaminated oil, through the use of continuous solvent extraction.

Streck et al., U.S. Pat. No. 4,776,947 discloses a method for dehalogenation of halogenated organic compounds in hydrocarbon oils through the use of alkali or alkaline earth alcoholates having at least 6 carbon atoms.

Many of the previous references have involved the use of a reagent derived from the reaction of an alkali metal or alkali metal hydroxide. These references teach the combination of such a reagent, in an amount at or above stoichiometric with respect to the total number of halogen groups, with a solution containing the contaminating halogenated hydrocarbon. Most teach the use of substantially elevated temperatures.

Airs et al., British Patent Specification 618,189 discloses dehydrohalogenation of dihalogen alkenes and monohalogen alkenes to produce alkynes through the use of glycol monoalkylether alcoholates.

SUMMARY OF THE INVENTION

This invention is directed toward an improved method for detoxifying waste materials containing halogenated hydrocarbons. More specifically the invention provides an improved chemical process for dehalogenating halogenated organic compounds.

An object of this invention is to provide an efficient and effective chemical process that will remove one or more halogens from a variety of halogenated organic compounds. For purposes of this invention, "substantially dehalogenate" means to remove one or more halogens from at least about 80 percent of the halogenated hydrocarbon molecules present.

Another object of the invention is to provide a process that is more cost effective than existing chemical processes for the dehalogenation of halogenated organic compounds.

Thus, an object of the invention is to identify a more efficient chemical reagent for such a process, thereby allowing a reduced amount of such a reagent to be used in the process. Additionally, an object of the invention is to provide a reagent that would allow the process to proceed at lower temperatures, without requiring the reaction to proceed for longer periods of time. The combined effect of reduced use of reagents and elimination or reduction of the need to heat the reaction mixture provides a substantial savings in cost without sacrificing effectiveness.

An embodiment of the invention provides for the dehalogenation of halogenated hydrocarbons present in a waste material through a method comprising the following steps:

(a) mixing the waste material comprising one or more halogenated organic compounds with a hydroxide of an alkali or alkaline earth metal or aluminum and 2-methoxyethanol, each present in amounts less than stoichiometric with respect to the total number of halogen groups present; and (b) incubating the mixture at temperatures from about 20° C. to about 130° C. for a period of time less than about 24 hours, yet sufficient to substantially dehalogenate the halogenated organic compounds present in the waste material.

Another embodiment of the invention provides for the preformation of a metal alcoholate derived from 2-methoxyethanol prior to incubation of such reagent with the contaminated waste material. This embodiment comprises the steps of:

(a) mixing together a hydroxide of an alkali or alkaline earth metal or aluminum with 2-methoxyethanol;

(b) incubating together the preparation of (a) at a temperature and for a time sufficient to allow substantially complete formation of a reagent comprising the metal alkoxide derivative of 2-methoxyethanol;

(c) adding the reagent from (b) to a waste material comprising one or more halogenated organic compounds, the reagent being present in an amount less than stoichiometric with respect to the total number of halogen groups present, thus forming a reaction mixture; and (d) incubating the reaction mixture at a temperature from about 20° C. to about 130° C. for a period of time less than about 24 hours and yet sufficient to substantially dehalogenate the halogenated organic compounds present in the waste material.

The present invention provides a more cost efficient means of dehalogenating halogenated hydrocarbons through the use of hydroxides of alkali or alkaline earth metals or aluminum, and 2-methoxyethanol in amounts less than stoichiometric with respect to the total amount of halogen groups present, as well as through the use of nonelevated or less elevated temperatures. The savings in reagent and energy are made possible through the discovery that 2-methoxyethanol surprisingly acts as a more effective reagent than does any other glycol monoalkyl ether under such conditions.

Specific preferred embodiments of the present invention will become evident from the following more detailed description of certain preferred embodiments and the claims.

DETAILED DESCRIPTION OF THE PREFERRED EMBODIMENTS

The present invention provides for the economical dehalogenation of halogenated hydrocarbons. Economy is achieved through the use of methods that utilize lower temperatures and/or smaller quantities of reagents than any existing procedure. This is made possible by utilizing the reagent 2-methoxy-ethanol, which is superior to prior specifically described reagents.

The method of the invention is effective for detoxifying soils or liquids that are contaminated with halogenated hydrocarbons by dehalogenating such halogenated hydrocarbons. A variety of halogenated hydrocarbons may be dehalogenated by the method of the invention, including, but not limited to PCBs, polybrominated biphenyls (PBBs), polychlorinated dibenzodioxins, polychlorinated dibenzofurans, halobenzenes, dichlorodiphenyltrichloroethane (DDT), ethylene dibromide, aldrin, dieldrin, toxaphene, and the like, or mixtures thereof. The contaminating halogenated hydrocarbons may be present in soils or liquids at concentrations from about 0.01% to about 100%. When contaminated liquids are used, the method of the invention may be practiced upon such liquids directly. When contaminated soils are to be treated, such soils will be first emulsified in a liquid and then treated by the method of the invention.

The contaminated substances are detoxified through the dehalogenation of the halogenated hydrocarbons. This is achieved through a reaction between the halogenated hydrocarbon and a metal alcoholate reagent derived from the reaction between 2-methoxyethanol and an alkali or alkaline earth metal or aluminum. Such a reagent can be represented by the structural formula $$M-(O-CH_2-CH_2-O-CH_3)_n$$

where M = an alkali metal selected from the group consisting of lithium, sodium potassium, rubidium and cesium and n = 1, or where M = an alkaline earth metal selected from the group consisting of magnesium, calcium, stronium and barium and n = 2, or where M = aluminum and n = 3.

The reaction between the above reagent and the halogenated hydrocarbon (R—X), results in the derivative $R-O-CH_2-CH_2-O-CH_3$ and M—X, where R represents the hydrocarbon and X represents the halogen.

The concentration of the alkali or alkaline earth metal or aluminum alcoholate of 2-methoxyethanol to be used will vary with the concentration of the contaminating halogenated hydrocarbons present in the soil or liquid to be treated. The ratio between the reagent and halogenated hydrocarbon may also vary. In a preferred embodiment, the molar concentration of such alkali or alkaline earth metal or aluminum alcoholate reagent of 2-methoxyethanol will not exceed the molar concentration of total halogen groups present in such halogenated hydrocarbons. Most preferred is a slightly less than stoichiometric ratio of the reagent and halogen, i.e., from about 65% to 90% of stoichiometric.

The method of the invention is carried out at temperatures, and for times sufficient to substantially dehalogenate the halogenated hydrocarbons present in the contaminated liquid or soil. The acceptable temperature range for substantial dehalogenation of halogenated hydrocarbons is from about 20° C. to about 135° C. Most preferred is a temperature of about 115° C. At temperatures above about 135° C., somewhat higher levels of dehalogenation will occur per unit of time, but with the sacrifice of economy afforded through the use of lower temperatures. Thus, higher temperatures are not preferred. The time for which the method is utilized to substantially dehalogenate halogenated hydrocarbons varies inversely with the temperature employed. In any case, such time should preferably not exceed about 24 hours. At the most preferred temperature, substantial dehalogenation (greater than 95% in this case) occurs within about five hours.

In a preferred embodiment of the invention, the formation of the alkali or alkaline earth metal or aluminum alcoholate of 2-methoxyethanol may take place as the reaction with the halogenated hydrocarbons proceeds, i.e., the hydroxide of an alkali or alkaline earth metal or aluminum, the 2-methoxyethanol, and the liquid containing the halogenated hydrocarbon may be added together at approximately the same time. In another preferred embodiment of the invention, the alkali or alkaline metal or aluminum alcoholate may be formed prior to the reaction with the halogenated hydrocarbon by mixing together the hydroxide of an alkali or alkaline earth metal or aluminum with the 2-methoxyethanol and incubating together at a temperature from about 20° C. to about 135° C. and for a time from about 15 minutes to about 9 hours, thus allowing formation of the metal alcoholate prior to the addition of the halogenated hydrocarbon.

The alkali metals used in the method of the invention include lithium, sodium, potassium, rubidium, and cesium. The alkaline earth metals used in the method of the invention include magnesium, calcium, strontium and barium. Alkali metals, alkaline earth metals and aluminum are each used in the metal hydroxide form for the purposes of the present invention. The overall molar quantities of metal hydroxide and 2-methoxyethanol are usually less than stoichiometric with respect to the total molar quantity of halogens present in the halogenated hydrocarbons and typically from about 25% to about 99% of stoichiometric.

The ability to use reagents in amounts less than stoichiometric with respect to the quantity of halogens present and the ability to practice the method of the invention at temperatures lower than those described for other dehalogenation processes without substantial loss of effectiveness, provides for an economical and useful alternative to previously accepted practices relating to the destruction of halogenated hydrocarbons. These unexpected features are made possible by the surprising discovery that the metal alcoholate of 2-methoxyethanol is a more efficient reagent for the dehalogenation of halogenated hydrocarbons than any other glycol monoalkyl ether. The use of other reagents that are chemically similar to 2-methoxyethanol results in a less efficient process. For example, with all other reaction conditions being equal, the substitution of 2-ethoxyethanol or 1-methoxy-2-propanol for 2-methoxyethanol, results in an increase in residual halogenated hydrocarbon of greater than 300-fold.

Reagents dissimilar to 2-methoxyethanol, but well known to be effective for dehalogenation of halogenated hydrocarbons, are also less efficient than 2-methoxyethanol. For example, with all other reaction conditions being equal, the substitution of polyethylene glycol for 2-methoxyethanol results in an increase in residual halogenated hydrocarbon.

Thus 2-methoxyethanol is more effective than previously recognized reagents for dehalogenation of halogenated hydrocarbons and is surprisingly far superior to chemically similar reagents.

The following examples are provided as means for illustration and are not limiting in nature:

EXAMPLE 1

A 500 ml three neck round bottom flask was equipped with a reflux condenser, heating mantle and magnetic stirrer. To the flask were added 18.15 g 1,3,5-trichlorobenzene (TCB), 15.22 g 2-methoxyethanol, 13.20 g potassium hydroxide, 3.86 g biphenyl (as an internal standard), and 30 ml toluene. The above were stirred and heated to reflux for a total of 6 hours. Samples were removed at hourly intervals, washed with water and dried over anhydrous magnesium sulfate. The samples were then analyzed by gas chromatography (gc). After one hour, 63% of the TCB had been destroyed. The identity of the product of the reaction, 3,5-dichloro-1-(2-methoxyethoxy)benzene, was confirmed by gas chromatography/mass spectrometry (gc/ms). After 5 hours, 99% of the TCB was converted, and within the next hour, the level of TCB was reduced to below the limit of detection (<0.1%).

COMPARATIVE EXAMPLE 2

A reaction of 18.15 g TCB was carried out as in Example 1, except that the 2-methoxyethanol was replaced with 18.02 g 2-ethoxyethanol. After 12 hours at reflux, 97% of the TCB was destroyed.

COMPARATIVE EXAMPLE 3

A reaction of 18.15 g TCB was carried out as in Example 1, except that the 2-methoxyethanol was replaced with 18.02 g 1-methoxy-2-propanol. After 12 hours at reflux, 69% of the TCB was destroyed.

EXAMPLE 4

A 250 ml three neck flask was equipped with reflux condenser, mechanical stirrer and thermometer. To the flask was added 40.00 g of a polychlorinated biphenyl (PCB)-contaminated transformer oil, which contained 256,600 ppm PCBs. To this was added, with stirring, 31.17 g 90% potassium hydroxide, 38.05 g 2-methoxyethanol, and 40.00 g of mineral oil as a solvent. The entire reaction mixture was heated in an oil bath with stirring to a temperature of 115°±5° C. for 5 hours. At the end of this period, a sample aliquot was removed, extracted with hexane/acetone (9:1), and further diluted with hexane, followed by a sulfuric acid wash and successive hexane dilutions. Analysis by gc revealed the PCBs concentration to be reduced to 4,600 ppm (98% PCB destruction).

EXAMPLE 5

To a 250 ml round bottom three neck flask equipped with mechanical stirrer, condenser and thermometer were added 31.17 g of potassium hydroxide and 38.05 g 2-methoxyethanol. These were heated to 115°±5° C. with stirring for 30 minutes to pre-form the potassium ethylene glycol monomethyl ether derivative (KGME, 57.09 g). The contaminated oil (40.00 g, 256,600 ppm PCBs) was added, and the reaction mixture continued to stir at 115°±5° C. for 5 hours. Analysis at the end of this period revealed that the PCBs concentration was reduced to 10,200 ppm (96% destruction of the PCBs).

COMPARATIVE EXAMPLE 6

The reaction of Example 5 was repeated using 57.09 g of the potassium derivative of polyethylene glycol 400 (KPEG, pre-formed from 52.13 g polyethylene glycol 400 and 7.31 g potassium hydroxide), in place of the KGME. At the end of 5 hours, 17,900 ppm PCBs remained (93% destruction of PCBs). Thus for equal weights of KGME vs KPEG, a known dehalogenation reagent, a significantly higher level of destruction of PCBs was obtained using KGME.

EXAMPLE 7

In a 250 ml round bottom three neck flask equipped with condenser, thermocouple and mechanical stirrer was added 102.0 g of a contaminated oil which contained 600,000 ppm PCBs, a total of 722 ppb polychlorinated dibenzodioxins (PCDDs, of which 40 ppb was attributed to the 2,3,7,8-tetrachloro isomer) and 2,725 ppb polychlorinated dibenzofurans (PCDFs). To this were added 77.6 g of 2-methoxyethanol and 39.8 g of potassium hydroxide. The reaction mixture was stirred and heated to 115°±1° C. for 5 hours. At the end of this time, an aliquot was removed for analyses of the PCBs, PCDDs and PCDFs. The PCBs concentration was reduced to 36,400 (95% destruction), while the PCDDs concentration was reduced to <4.5 ppb (>99.4% destruction of dioxins, of which the 2,3,7,8-tetrachloro isomer was reduced to below the limit of detection, i.e. <1 ppb). The PCDFs concentration was reduced to 3 ppb (99.9% destruction).

EXAMPLE 8

A 250 ml three neck flask was equipped with a reflux condenser, mechanical stirrer and thermometer. To the flask was added 100.00 g of a polychlorinated biphenyl (PCB)-contaminated transformer oil, which contained 256,600 ppm PCBs (about 1:1:3 of aroclors 1242, 1254 and 1260, respectively). To this was added, with stirring, 38.44 g 2-methoxyethanol and 33.27 g 90% potassium hydroxide. The entire reaction mixture was heated in an oil bath with stirring, to a temperature of 115°±5° C. for 3.5 hours. An exotherm to about 135° C. occurred within fifteen minutes of initial heating, but the internal reaction temperature fell to 115° C. within the following half hour. At the end of the 3.5 hour period, a sample aliquot was removed, extracted with hexane/acetone (9:1), and further diluted with hexane, followed by a sulfuric acid wash and successive hexane dilutions. Analysis by gc (ecd) indicated a reduction of total aroclors to 45,200 ppm, with aroclors 1254 and 1260 being reduced below the limits of detection.

We hereby claim:

1. A method for dehalogenating a halogenated organic compound, said method comprising the following steps:

(a) providing a reaction mixture comprising a waste material comprising the halogenated organic compound, a hydroxide of a metal selected from the group consisting of lithium, sodium, potassium, rubidium, cesium, magnesium, calcium, strontium, barium, and aluminum, and 2-methoxyethanol, and (b) incubating the reaction mixture at a temperature from about 20° C. to about 135° C. for a period of time sufficient to substantially dehalogenate the halogenated organic compound, the period of time being less than about 24 hours.

2. A method for dehalogenating a halogenated organic compound, said method comprising the following steps:

(a) mixing together 2-methoxyethanol and a hydroxide of a metal selected from the group consisting of lithium, sodium, potassium, rubidium, cesium, magnesium, calcium, strontium, barium and aluminum;

(b) incubating the metal hydroxide and 2-methoxyethanol together for a time and at a temperature sufficient to form a reagent comprising a metal alcoholate derived from 2-methoxyethanol;

(c) mixing the metal alcoholate reagent together with a waste material comprising the halogenated organic compound to form a reaction mixture;

(d) incubating the reaction mixture at a temperature from about 20° C. to about 135° C. for a period of time sufficient to substantially dehalogenate the halogenated organic compound, the period of time being less than about 24 hours.

3. A method according to claim 1, wherein the metal hydroxide and the 2-methoxyethanol are present in an amount less than stoichiometric relative to the number of halogen groups present.

4. A method according to claim 2, wherein the metal alcoholate reagent is present in the reaction mixture in an amount less than stoichiometric with respect to the number of halogen groups present.

* * * * *